(12) United States Patent
Van Acht et al.

(10) Patent No.: US 8,743,054 B2
(45) Date of Patent: Jun. 3, 2014

(54) GRAPHICAL REPRESENTATIONS

(75) Inventors: Victor Martinus Gerardus Van Acht, Eindhoven (NL); Nicolaas Lambert, Eindhoven (NL); Edwin Garardus Johannus Maria Bongers, Eindhoven (NL); Juergen Te Vrugt, Aachen (DE); Richard Daniel Willmann, Siegburg (DE); Gerd Lanfermann, Aachen (DE); Declan Patrick Kelly, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 312 days.

(21) Appl. No.: 13/132,626

(22) PCT Filed: Dec. 3, 2009

(86) PCT No.: PCT/IB2009/055481
§ 371 (c)(1),
(2), (4) Date: Jun. 3, 2011

(87) PCT Pub. No.: WO2010/067275
PCT Pub. Date: Jun. 17, 2010

(65) Prior Publication Data
US 2011/0234489 A1    Sep. 29, 2011

(30) Foreign Application Priority Data
Dec. 10, 2008    (EP) ...................................... 08171164

(51) Int. Cl.
*G06F 3/033*    (2013.01)

(52) U.S. Cl.
USPC ............................................ 345/158; 345/156

(58) Field of Classification Search
USPC ............................................................ 345/158
See application file for complete search history.

(56) References Cited

U.S. PATENT DOCUMENTS

| | | |
|---|---|---|
| 5,570,301 A | 10/1996 | Barrus |
| 6,115,025 A | 9/2000 | Buxton et al. |
| 7,184,025 B2 | 2/2007 | Williams et al. |
| 2001/0031081 A1 | 10/2001 | Quan |
| 2002/0103610 A1 | 8/2002 | Bachmann et al. |
| 2004/0131247 A1 | 7/2004 | Hiwada |
| 2007/0032748 A1 | 2/2007 | McNeil et al. |
| 2007/0038944 A1* | 2/2007 | Carignano et al. ............. 715/757 |
| 2009/0002391 A1* | 1/2009 | Williamson et al. .......... 345/619 |

FOREIGN PATENT DOCUMENTS

| | | | |
|---|---|---|---|
| JP | 2005092657 A | | 4/2005 |
| WO | 03001248 A2 | | 1/2003 |
| WO | 2007093641 A2 | | 8/2007 |
| WO | WO 2008/099301 A1 * | | 8/2008 |

* cited by examiner

*Primary Examiner* — Alexander Eisen
*Assistant Examiner* — Robin Mishler

(57) ABSTRACT

A controller for a display device includes a processor configured to receive an indication of the orientation of a user of the display device; receive an indication of the orientation of the display device; and generate a graphical representation of a user of the display device using the received indications, such that the orientation of the graphical representation of the user is adapted based on the orientation of the display device.

17 Claims, 5 Drawing Sheets

GRAPHICAL REPRESENTATIONS

TECHNICAL FIELD OF THE INVENTION

The invention relates to graphical representations, and in particular to graphical representations of users, otherwise known as avatars.

BACKGROUND TO THE INVENTION

Recently, there have been efforts to develop systems to help in the rehabilitation of people who have suffered an injury or disability (for example due to a stroke), and in particular to provide systems that can instruct the user to perform particular exercises, monitor the movements of the different parts of the user's body and provide useful feedback to the user on their movements, without requiring a physiotherapist or other professional to be present. Of course, these systems can also be used in the presence of a physiotherapist or other professional to help them provide effective therapy to the user.

Typically, users will spend a lot of time practicing basic exercises. This leads to frustration for the users because it is difficult to see the relation between the basic exercises that they need to practice and the activities of daily life that they want to recover. Without seeing this connection, users can become de-motivated in practicing the basic exercises.

In order to motivate users to perform basic exercises, the user should understand the relation between the basic exercises and the final goal. Users that have suffered a stroke often have cognitive difficulties as well as physical problems, so it is desirable to present the link between basic exercises and final goals in an intuitive way.

Feedback and instructions to the user can be provided, at least in part, by a graphical representation of the user on a display device. This graphical representation can provide a computer-generated image of the user, so that the user can see whether their movement and posture is correct. The graphical representations provide the advantage that it is possible for the user to see their own movements from different view points (for example, the graphical representation can be a mirror image, a true (non-mirrored) image, a view from the side, etc.). These graphical representations are often known as avatars.

Parts of the user's body can be monitored by respective sensor units that include motion sensors (such as accelerometers, magnetometers and gyroscopes) that measure the position and motion of the part of the body in a world coordinate frame of reference. Normally at least five sensor units are required, attached, respectively, to the chest and upper and lower arms. This allows the avatar to represent the movement and posture of the upper half of the user's body.

Additional sensor units can be attached to the legs to allow the avatar to represent the whole of the user's body. Clearly, the more sensor units that are placed on the user's body, the more accurate the avatar can be.

However, a problem arises in that the algorithm that creates the graphical representation of the user from the sensor unit data has no knowledge of the orientation or position of the display device, which means that it is difficult to use the display device as, say, a virtual mirror (so that when the user faces the display device, the graphical representation of the user faces the user).

If no action is taken, this desired situation is only reached for a single arrangement of the display device. FIG. 1 shows an example of this particular arrangement. Here, the user 2 is facing a display device 4. The user is facing north, and the display screen 5 of the display device 4 is oriented along an east-west axis, with the display screen 5 facing south. A number of sensor units 6 are attached to the user 2 for measuring the position and motion of the user 2.

The algorithm that creates the graphical representation 8 is configured so that the graphical representation 8 faces out of the display device 4 when the user 2 is facing north (as measured by the magnetometer(s) in the sensor units 6).

However, as shown in FIG. 2, if the display device 4 is not oriented along an east-west axis, the graphical representation 8 created using the same algorithm will not be a mirror image of the user 2.

In particular, the display device 4 is oriented along a north-south axis with the display screen 5 of the display device 4 facing west. As the user 2 is now facing east, the algorithm creates the graphical representation 8 that is turned to the left on the display screen 5 (i.e. facing south).

This problem results from the orientation of the user 2 being measured in a world-fixed frame of reference by the magnetometers (otherwise known as electronic compasses) in the sensor units 6.

One approach to get around this problem is to provide a control for setting the compass rotation of the graphical representation 8 manually.

Another option is to calibrate the algorithm with respect to the orientation or position of the display device 4. Typically, this is done by getting the user 2 to face the display device 4, and using the orientation (magnetometer) measurement from the sensor units 6 to calibrate the algorithm. Only after this initial measurement is taken can the graphical representation 8 be correctly displayed on the display screen 5.

However, it is desirable to provide a solution to this problem that does not require manual action or calibration by the user.

SUMMARY OF THE INVENTION

According to a first aspect of the invention, there is provided a controller for a display device, the controller comprising a processor configured to receive an indication of the orientation of a user of the display device; receive an indication of the orientation of the display device; and generate a graphical representation of a user of the display device using the received indications, such that the orientation of the graphical representation of the user is adapted based on the orientation of the display device.

Preferably, the processor is configured to generate a graphical representation from the received indication of the orientation of the user that is rotated by an angle given by the received indication of the orientation of the display device.

Even more preferably, the processor is configured to generate a graphical representation from the received indication of the orientation of the user that is rotated around a vertical axis of the graphical representation by an angle given by the received indication of the orientation of the display device.

In some embodiments, the processor is configured to generate a graphical representation of the user that is a mirror image of the user when displayed on the display device.

In these embodiments, the processor is preferably configured to mirror the graphical representation prior to display of the graphical representation by the display device.

Preferably, the orientations are given with respect to a predetermined direction. In a preferred embodiment, the predetermined direction is magnetic north. In some embodiments, the orientations are given in three dimensions.

In further embodiments, the processor is further configured to receive indications of the movement and/or posture of the user, and to generate the graphical representation such that the graphical representation corresponds to the indicated movement and/or posture of the user.

In yet further embodiments, the processor is further configured to animate the graphical representation to demonstrate movements and/or postures to the user when the graphical representation is displayed on a display device.

In these embodiments, the processor is preferably configured to animate the graphical representation to demonstrate a plurality of basic movements that together form a complex movement, each basic movement comprising the movement of a single joint in the graphical representation of the user.

Preferably, the processor is configured to generate first and second graphical representations, with the first graphical representation being animated to demonstrate the plurality of basic movements, and the second graphical representation being animated to demonstrate the complex movement.

In some embodiments, the processor is configured to animate the graphical representation to indicate a current ability of the user relative to a desired ability.

A second aspect of the invention provides a display device, comprising a sensor for determining the orientation of the display device and a controller as described above.

Preferably, the sensor is a magnetometer. In further embodiments, the sensor further comprises an accelerometer.

A third aspect of the invention provides a method of generating a graphical representation of a user for display on a display device, the method comprising receiving an indication of the orientation of the user of the display device; receiving an indication of the orientation of the display device; and generating a graphical representation of the user of the display device using the received indications, such that the orientation of the graphical representation of the user is adapted based on the orientation of the display device.

A fourth aspect of the invention provides a computer program product comprising computer program code that, when executed on a suitable computer or processor, is adapted to perform the steps in the method described above.

BRIEF DESCRIPTION OF THE DRAWINGS

The invention will now be described, by way of example only, with reference to the following drawings, in which.

DETAILED DESCRIPTION OF THE PREFERRED EMBODIMENTS

Although the invention will be described below with reference to a rehabilitation or exercise system, it will be appreciated that the invention can be applied to any system in which a graphical representation of a user or avatar is to be generated from sensor data measured in a world coordinate frame of reference. For example, the invention can be applied in a computer games console or in a general purpose computer.

Figure 1:
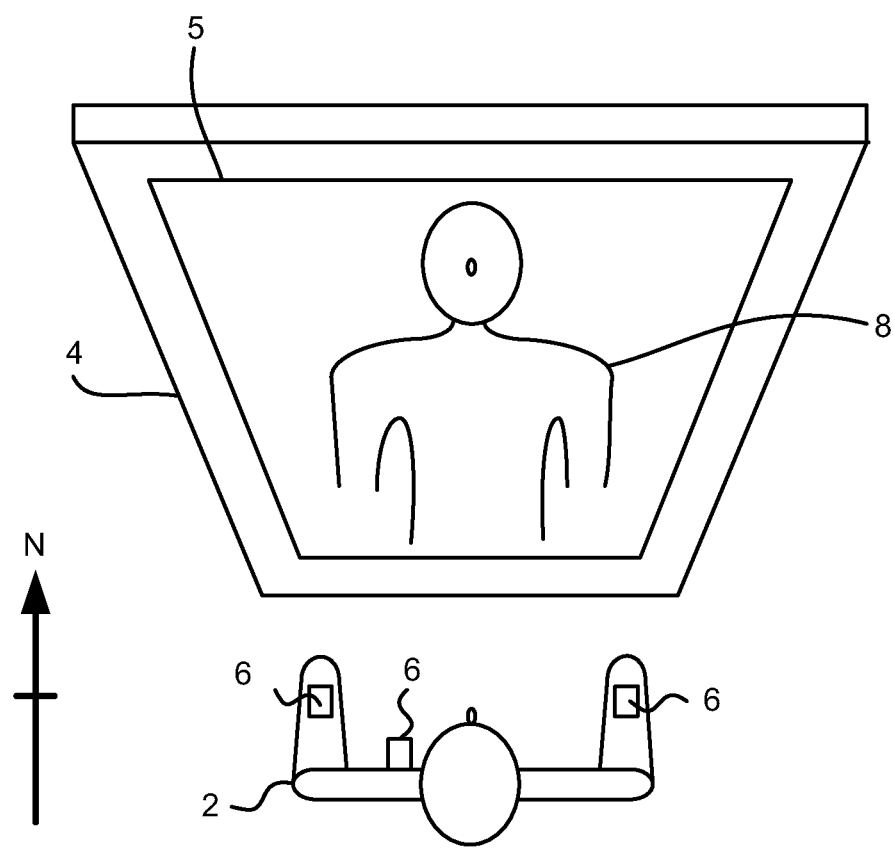
FIG. 1 shows a user and a display device in a first arrangement.
Figure 2:
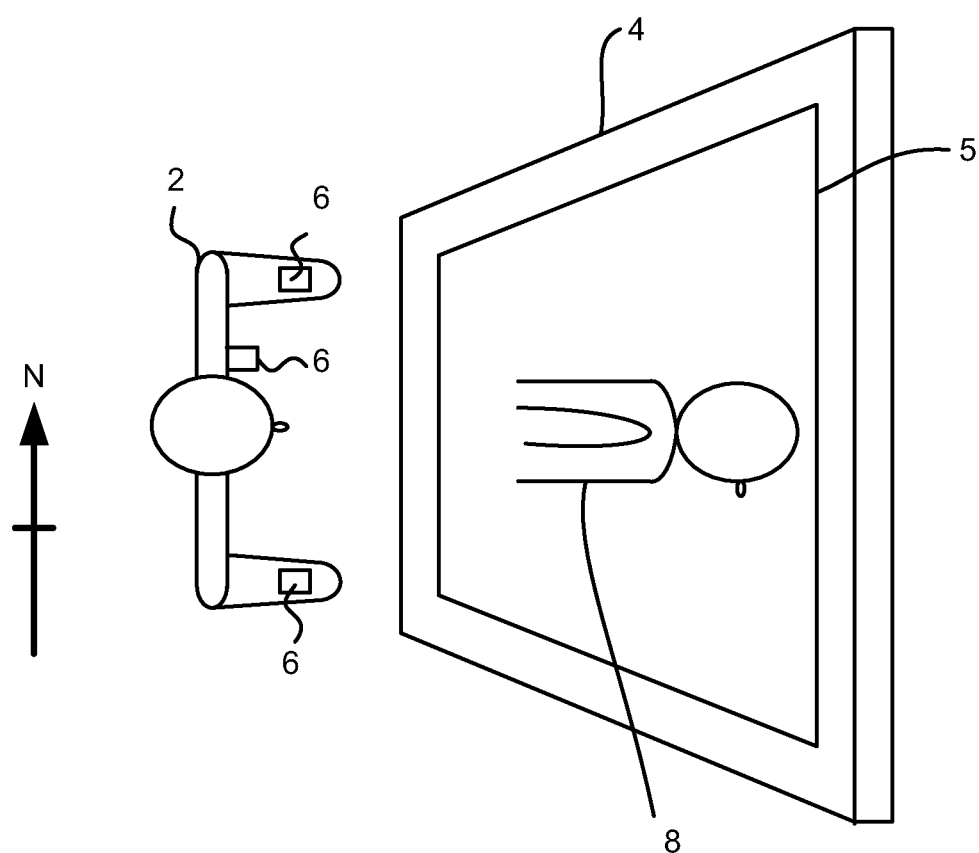
FIG. 2 shows a user and a display device in a second arrangement.
Figure 3:
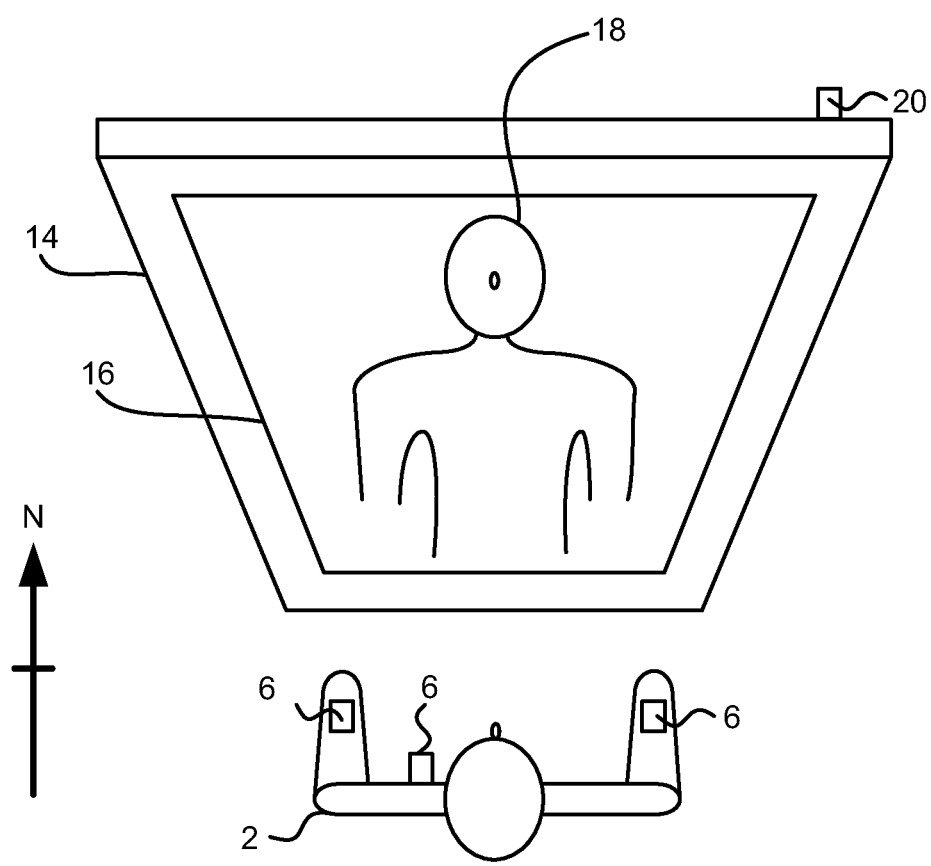
FIG. 3 shows a user and a display device in accordance with a first embodiment of the invention.

FIG. 3 shows a display device 14 in accordance with the invention. As before, a user 2 is provided with a number of sensor units 6 that monitor the position and movement of parts of the body of the user 2. The data collected by the sensor units 6 is transmitted wirelessly to the display device 14. In a preferred embodiment, the sensor units 6 include an accelerometer for measuring the movement of the user 2, and a magnetometer for measuring the orientation of the user 2 with respect to magnetic north.

In alternative embodiments, the sensor units 6 can be replaced by a visual tracking system that observes the user 2 and determines the orientation and movement of the user 2 from the obtained images.

The display device 14 comprises a display screen 16 that provides images, including the graphical representation 18 of the user 2. However, in accordance with the invention, the display device 14 is provided with an orientation sensor 20 that measures the direction in which the display device 14 (and hence the display screen 16) is facing. In a preferred embodiment, the orientation sensor 20 measures the orientation of the display device 14 with respect to magnetic north.

It will be appreciated that the orientation of the user 2 or display device 14 can be determined using any suitable sensor or sensor system. For example, in alternative embodiments, it is possible to determine the orientation of the user 2 or display device 14 using radar, sonar, Doppler or potentiometers.

Thus, as the orientation of the display device 14 is known from the orientation sensor 20, the algorithm used to generate the graphical representation 18 can generate the graphical representation 18 of the user 2 from the data from the sensor units 6, and rotate the generated graphical representation 18 for display to the user 2, such that the displayed graphical representation 18 is facing in a required direction.

For example, where the algorithm is to generate a graphical representation 18 of the user 2 that it is a mirror image of the user 2 (so for example the avatar 18 is facing the user 2 when the user 2 is facing the display device 14 and movement of the left arm of the user 2 is shown by movement of the right arm of the avatar 18), the algorithm generates the graphical representation 18 from the data from the sensor units 6, rotates the graphical representation 18 using the determined orientation of the display device 14, and mirrors the graphical representation 18 about a vertical axis such that the displayed graphical representation 18 is a mirror image of the user 2.

In alternative embodiments, the algorithm can provide a non-mirrored graphical representation 18 of the user 2 (for example as though a camera was mounted on the display device 14), or any other desired orientation of the user 2 (for example the avatar 18 may show the user 2 from the side), using the measured orientation of the display device 14.

Therefore, regardless of the orientation of the display device 14 (with respect to magnetic north), the invention provides that the avatar 18 shown on the display screen 16 will be adapted so that it faces in a required direction.

Figure 4:
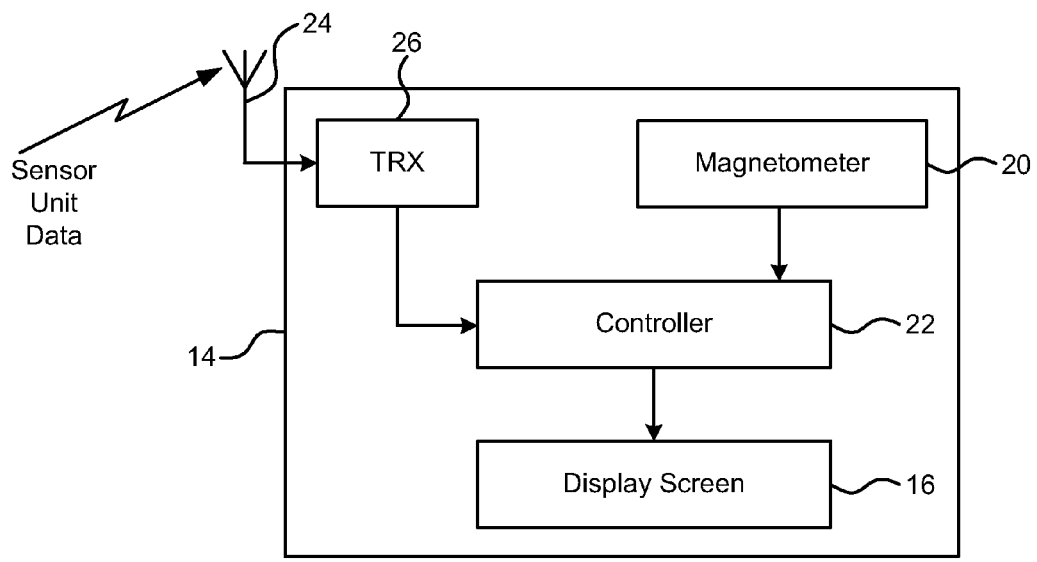
FIG. 4 is a block diagram of a display device in accordance with an embodiment of the invention.

FIG. 4 shows the display device 14 in more detail. The display device 14 comprises a controller 22 for controlling the operation of the display device 14 and for generating the graphical representation 18 from the sensor unit data. The controller 22 receives the indication of the orientation of the display device 14 from the orientation sensor 20 (a magnetometer in this embodiment) and the sensor unit data from the user 2 via an antenna 24 and transceiver or receiver circuitry 26. The controller 22 also provides the image data for the graphical representation 18 to the display screen 16.

It will be appreciated that, in alternative embodiments, the graphical representation 18 can be generated by a controller or processor that is separate to the display device 14.

The operation of the controller 22 in adapting the graphical representation 18 of the user 2 will now be described in more detail with reference to FIGS. 5 and 6.

Figure 5:
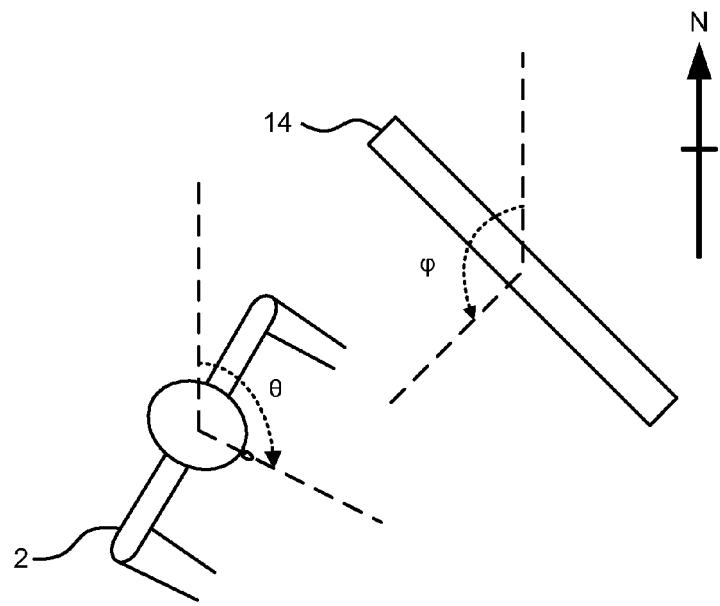
FIG. 5 is an illustration of a user and a display device.

In FIG. 5, a user 2 is shown oriented at an angle θ with respect to magnetic north (with θ defined to be 0 when the user 2 is facing north, positive when the user 2 turns anticlockwise, and negative when the user 2 turns clockwise). The display device 14 is shown oriented at an angle φ with respect to magnetic north (with φ defined in the same way as θ).

An angle α is also defined as θ-φ. The controller 22 uses α to determine the orientation of the graphical representation 18. When α is 0, the controller 22 generates the graphical representation 18 such that it faces into the display device 14 (i.e. the back of the user 2 is shown by the graphical representation 18).

The controller 22 is also configured such that when α is positive, the graphical representation 18 is rotated anticlockwise about a vertical axis (i.e. the graphical representation 18 of the user 2 is turned to the left) by angle α, and when α is negative, the graphical representation 18 is rotated clockwise about a vertical axis (i.e. the graphical representation 18 of the user 2 is turned to the right) by angle α.

Thus, in the example shown in FIG. 3, the angle θ is 0 (the user 2 is facing north), the angle φ is 180° (the display device 14 is facing south), so α is 180°. Thus, the controller 22 will rotate the graphical representation 18 180° so that it faces out of the display device 14 towards the user 2.

To generate a mirror image of the user 2, the rotated graphical representation 18 can be flipped about a vertical axis by the controller 22.

Figure 6:
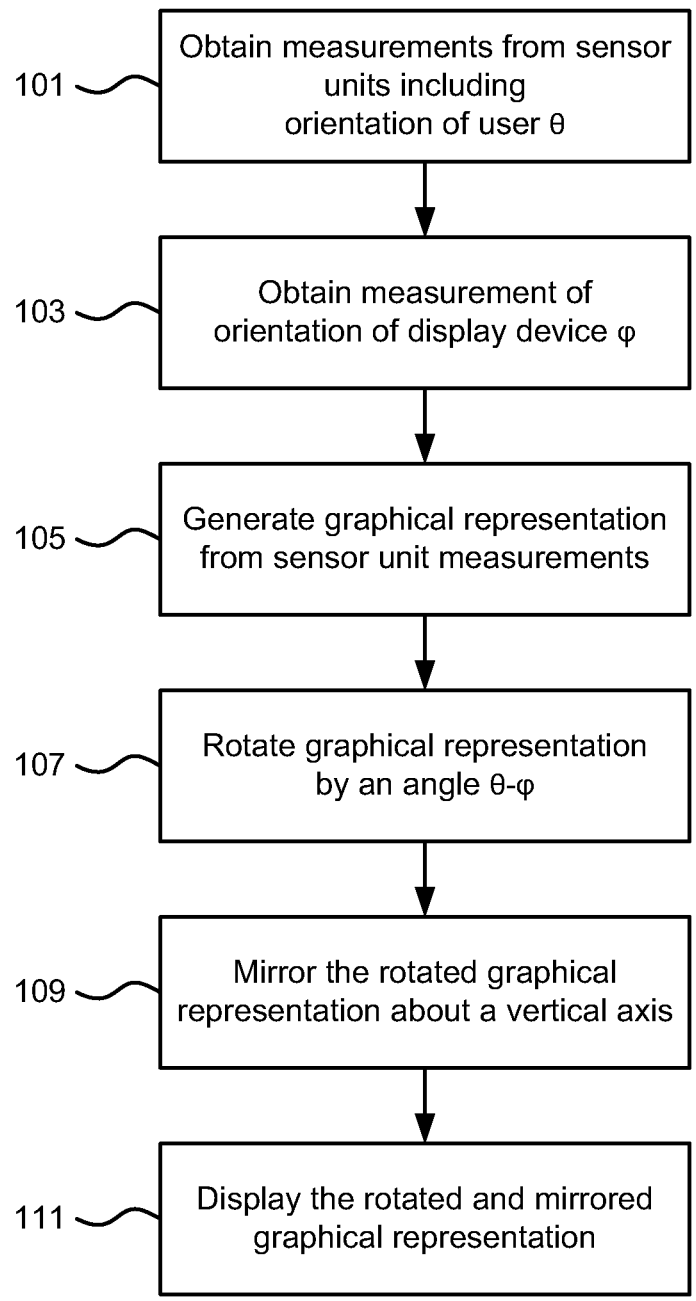
FIG. 6 is a flow chart illustrating the steps in a method in accordance with the invention.

In step 101 of FIG. 6, measurements of the orientation of the user, in terms of an angle θ with respect to magnetic north, are obtained from the sensor units 6, along with measurements of the posture and position of the body of the user.

In step 103, a measurement of the orientation of the display device, in terms of an angle φ with respect to magnetic north, are obtained from the magnetometer 20.

In step 105, a graphical representation of the user is generated from the measurements from the sensor units 6.

In step 107, the graphical representation is rotated around a vertical axis by an angle θ-φ, so that the graphical representation, when displayed on the display screen, faces in a desired direction.

In step 109, the mirror image is obtained by flipping or mirroring the rotated graphical representation about a vertical axis.

In step 111, the rotated and flipped/mirrored graphical representation is displayed on the display screen.

It will be appreciated that it is possible for steps 105, 107 and 109 to be combined into a single step in which the controller generates the graphical representation in the desired rotated and flipped/mirrored orientation.

It will also be appreciated that, in some of the embodiments described above (particularly the embodiments in which magnetometers or electronic compasses are used), the invention is primarily concerned with the orientation of the user 2 and display device 14 about a vertical axis. However, it will be appreciated that the invention can also be used to adapt the graphical representation 18 for any three-dimensional orientation of the user 2 and/or display device 14. Thus, in these embodiments, it is necessary to measure the orientation of the user 2 and display device 14 in three dimensions. This can be done, for example, by using a magnetometer for measuring the orientation with respect to magnetic north and an accelerometer for measuring orientation with respect to the vertical (given by gravity). Alternatively, a 3D camera tracking system can identify the orientation of the user 2.

In further embodiments of the invention, the displayed avatar 18 can be used to show how basic movements (for example comprising the movement of a single joint) combine to form complex movements. Thus, when the avatar 18 is used in this way, the avatar 18 will not be a true representation of the user 2, and will not necessarily be formed using all of the data from the sensor units 6. However, the displayed avatar 18 can still be oriented so that it corresponds to the orientation of the user 2 (so the avatar can still mirror the direction in which the user 2 is facing, for example).

In addition, the avatar 18 can be used to show which parts of the complex movements the user is able to perform and which parts the user still needs to practice and improve. In this embodiment, the controller 22 can obtain data on the previous performance of the user 2 from a memory, and can generate and animate the graphical representation 18 accordingly. The avatar 18 can also be used to show the user 2 how their progress on the basic exercises contributes to improving their ability to do the complex daily movements.

In one embodiment, the controller 22 can animate the avatar 18 to show the user 2 the full complex movement, and then the separate basic movements that make up the complex movement.

In an alternative embodiment, the controller 22 can display at least two avatars 18 at any given time, with the first avatar 18 showing the full complex movement and the second avatar 18 showing a particular basic movement. The two avatars 18 can be synchronised so that the avatar 18 showing the particular basic movement only moves during the corresponding part of the complex movement shown by the other avatar 18.

In an embodiment, the avatar 18 can be used to illustrate to the user 2 their current progress. For example, the avatar 18 can show the user 2 the parts of the complex movement that they are able to perform, and which parts require further practice.

This can be achieved by, for example, using colour to highlight the parts of the complex movement the user 2 can do, that is, use one colour (e.g. green) for the part of the complex movement the user 2 can do and a contrasting colour (e.g. red) to highlight the parts that cannot be done and therefore need further training Alternatively, the avatar 18 can be animated to show how much of the full complex movement the user 2 is able to perform, i.e. the avatar 18 will illustrate the full complex movement sequence, but only to the extent that the user 2 is able to do it (i.e. the parts the user 2 can do and the range of motion available to the user 2). In this embodiment, it is possible to show two avatars 18, one illustrating the full complex movement, and the other showing the user's current ability.

As an example, a complex movement, such as eating with a knife or fork, can be broken down into component parts, such as:

1) Reaching for the knife and fork—this requires elevation/protraction of the shoulder, flexion/extension of the elbow, opening of the fingers, anteflexion of the shoulder, further extension of the elbow, and calibration of the grasp width.

2) Grasping knife and fork—this requires a static shoulder and elbow region, ulna deviation, the wrist closing fingers to the opposite thumb, calibration of the grasp width (flexion of the thumb)

3) Lifting knife and fork—this requires a static shoulder, flexion of the elbows, wrist movement and grasp width calibration.

4) Moving food on the plate and lifting food to one quarter of the way to the mouth—this requires a small adduction of the shoulder, static/flexion/extension of the elbow and grasping, supinating the wrist and pronating the elbow.

5) Food to the mouth—this requires a small elevation of the shoulders and flexion/ extension movements of the elbows), supinating and pronating movements of the elbows and wrists, and calibration of grasp width.

There is therefore provided a system and method that allows a display of a graphical representation of a user, regardless of the position and orientation of the display device. Furthermore, there is provided a system and method that can provide avatars that motivate a user to continue with a particular exercise program.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope. A computer program may be stored/distributed on a suitable medium, such as an optical storage medium or a solid-state medium supplied together with or as part of other hardware, but may also be distributed in other forms, such as via the Internet or other wired or wireless telecommunication systems.

The invention claimed is:

1. A controller for a display device, the controller comprising:
    a processor configured to
    receive a first angle of orientation of a user of the display device with respect to a magnetic north and a second angle of orientation of the display device with respect to the magnetic north; and
    generate a graphical representation of the user such that the orientation of the graphical representation of the user is based on a difference between the second and first angles,
    wherein when the difference is 0 the graphical representation is a back of the user.

2. The controller as claimed in claim 1, wherein the received orientation of the user is rotated around a vertical axis of the graphical representation by the second angle.

3. The controller as claimed in claim 1, wherein the graphical representation of the user is a mirror image of the user when displayed on the display device.

4. The controller as claimed in claim 3, wherein the graphical representation is mirrored prior to display by the display device.

5. The controller as claimed in claim 1, wherein the orientations of the user and the display device are given with respect to a predetermined direction.

6. The controller as claimed in claim 5, wherein the predetermined direction is magnetic north.

7. The controller as claimed in claim 1, wherein the orientations of the user and the display device are given in three dimensions.

8. The controller as claimed in claim 1, wherein the processor is further configured to receive a movement and/or posture of the user, and to generate the graphical. representation that corresponds to the movement and/or posture of the user.

9. The controller as claimed in claim 1, wherein the processor is further configured to animate the graphical representation to demonstrate movements and/or postures to the user when the graphical representation is displayed on a display device.

10. The controller as claimed in claim 9, wherein the movements comprise a plurality of basic movements that together form a complex movement, each basic movement comprising the movement of a single joint.

11. The controller as claimed in claim 10, wherein the graphical representation comprises first and second graphical representations, the first graphical representation being animated to demonstrate the plurality of basic movements, and the second graphical representation being animated to demonstrate the complex movement.

12. The controller as claimed in claim 9, wherein the graphical representation is animated to indicate a current ability of the user relative to a desired ability.

13. The controller as claimed in claim 1, wherein the display device includes a sensor for determining the orientation of the display device.

14. The controller as claimed in claim 13, wherein the sensor is a magnetometer.

15. The controller as claimed in claim 14, wherein the sensor further comprises an accelerometer.

16. A method of generating a graphical representation of a user for display on a display device, the method comprising acts of:
    receiving a first angle of orientation of the user of the display device with respect to a magnetic north and a second angle of orientation of the display device with respect to the magnetic north; and
    generating a graphical representation of the user such that the orientation of the graphical representation of the user is based on a difference between the second and first angles,
    wherein when the difference is 0 the graphical representation is a back of the user.

17. A non-transitory computer readable medium comprising computer program code that, when executed on a processor, performs a method of generating a graphical representation of a user for display on a display device, the method comprising:
    receiving a first angle of orientation of the user of the display device with respect to a magnetic north and a second angle of orientation of the display device with respect to the magnetic north; and
    generating a graphical representation of the user, such that the orientation of the graphical representation of the user is based on a difference between the second and first angles,
    wherein when the difference is 0 the graphical representation is a back of the user.

* * * * *